United States Patent [19]

Maystre et al.

[11] Patent Number: 5,290,520
[45] Date of Patent: Mar. 1, 1994

[54] ANALYTIC SEPARATION ARRANGEMENT AND METHOD FOR THE ANALYSIS OF CHEMICAL SAMPLES

[75] Inventors: Francois Maystre, Reinach; Alfredo E. Bruno, Oberwil, both of Switzerland

[73] Assignee: Ciba-Geigy Corporation, Ardsley, N.Y.

[21] Appl. No.: 990,213

[22] Filed: Dec. 14, 1992

[30] Foreign Application Priority Data

Dec. 19, 1991 [DE] Fed. Rep. of Germany ..... 91810991

[51] Int. Cl.$^5$ ..................... G01N 21/01; G01N 30/74
[52] U.S. Cl. .................................... 422/82.05; 422/70; 422/82.08; 422/82.09; 422/89; 422/91; 73/23.4; 73/61.57; 73/61.58; 356/72; 356/410; 356/436
[58] Field of Search ............. 422/70, 82.05, 82.08, 422/82.09, 89, 91, 101; 73/61.57, 61.58, 23.4; 356/72, 410, 411, 436, 440

[56] References Cited

U.S. PATENT DOCUMENTS

| | | | |
|---|---|---|---|
| 4,019,372 | 4/1977 | Parkell et al. | 73/61.57 |
| 4,042,304 | 8/1977 | Martin et al. | 73/61.58 |
| 4,199,260 | 4/1980 | Kusnetz et al. | 73/23.4 |
| 4,403,503 | 9/1983 | Banerjee et al. | 73/61.58 |
| 4,659,934 | 4/1987 | Allington | 250/458.1 |
| 4,795,262 | 1/1989 | Morris et al. | 356/410 |
| 4,989,974 | 2/1991 | Anton et al. | 356/246 |
| 4,990,250 | 2/1991 | Hellinger | 422/70 |

FOREIGN PATENT DOCUMENTS 0164080 12/1985 European Pat. Off. .

OTHER PUBLICATIONS

Analytical Chemistry, 63, No. 5, Mar. 1991, pp. 490–496.
Analytical Chemistry, 63, No. 6, Mar. 1991, pp. 568–574.
Derwent Publications Ltd., 85-111709/19.
Analytical Chemistry, 1991, 63, 2689–2697.
Prospectus "Visco Mixer" by Breckbuehler AG, Switzerland, pp. 67–69.
CA 116(18):187298g.
CA 116:187923g.
Bruno et al., "On–Column Capillary Flow Cell Utilizing Optical Waveguides for Chromatographic Applications", Anal. Chem., vol. 61, pp. 876–883, 1989.

*Primary Examiner*—James C. Housel
*Assistant Examiner*—Jan M. Ludlow
*Attorney, Agent, or Firm*—Marla J. Mathias; William A. Teoli

[57] ABSTRACT

An analytic separation arrangement includes a system of tubes including a separation zone, preferably a separation column, which tubes upstream the separation zone are connected with reservoirs for a carrier and a chemical sample to be seperated and analyzed, and downstream the separation zone are connected with a waste container for the carrier containing the sample and also are connected with transporting means for the carrier and the sample. The tube system is associated with an optical detector for monitoring changes in the absorption, in the fluorescence or in the optical activity of the carrier when it is transported through the tube system and past the optical detector, which is arranged in the path of the carrier behind the separation zone but in front of the waste container. Between the separation zone and the optical detector there is arranged in the path of the carrier a refractive index equalizing unit. Prior to being transported past the optical detector the carrier, which is comming from the separation zone, is directed through the refractive index equalizing unit, where its refractive index is preferably constantly monitored and where upon detection of changes of the refractive index of the carrier the deviation is compensated by adding to the carrier a compensating agent.

9 Claims, 3 Drawing Sheets

ANALYTIC SEPARATION ARRANGEMENT AND METHOD FOR THE ANALYSIS OF CHEMICAL SAMPLES

BACKGROUND OF THE INVENTION

The invention relates to a method for the analysis of chemical samples according to the preamble of claim 1. The invention also relates to a separation arrangement as used for example in high performance liquid chromatography (HPLC) according to the preamble of claim 4.

In the field of modern chemical analysis various chromatographic techniques are employed for their high separation efficiencies. Thus separation methods such as gas chromatography, microbore liquid chromatography, capillary supercritical fluid chromatography, capillary zone electrophoresis and high performance liquid chromatography are most commonly used. Associated with the separation systems are various kinds of different detectors. For example in high performance liquid chromatography the most popular detectors are the ones, which employ optical detection methods to measure changes in the absorption, in the luminescence, more particularly in the fluorescence, in the optical activity in general or in the refractive index of the carriers. As a major drawback the changes in absorption, in fluorescence or in optical activity, which are to be detected, are very often associated with changes of the refractive index of the carrier.

The change of the refractive index of the carrier results very often in a non-linear response of the detector, in an increased noise level or even in a spurious response of the detector. It is apparent that these effects are detrimental to the quality of the analysis of a chemical sample and in some cases render quantitative evaluations of chromatograms impossible. Aware of these drawbacks instrument-manufacturers have tried to solve these problems by improving the design of such separation systems and of the associated detector cells as outlined e.g. in an article by A. E. Bruno in Analytical Chemistry 1989, 61, pages 876 to 883. Now, while the approach of the instrument-manufacturers has had some success in reducing the influences of refractive index changes the problem still has not been satisfactorily resolved and to date no truly refractive index insensitive separation system has been designed. In their article Bruno et. al. also point out that the disturbing refractive index effects are partially a result of a complex dynamic distortion of the optical path, due for example to Schlieren effects, which make it even more difficult to obtain a proper correction of the distorted chromatograms.

It is therefore an object of the instant invention to avoid these drawbacks of the prior art separation methods and the respective prior art separation systems. In particular it is an object to eliminate the detrimental effects due to variations of the refractive index of the carrier during the separation.

All these and still further objects are achieved by a separation method comprising the steps outlined in the second part of claim 1 and by an analytic separation arrangement comprising the features claimed in claim 4.

The object is solved in particular by a separation method for the analysis of chemical samples, wherein a chemical sample is introduced into a carrier, which is transported through a system of tubes and past an optical detector, and together with the carrier is transported through a separation zone, preferably a separation column, and wherein after passing the separation column the carrier and the sample, which then is separated into its components, are transported past the optical detector, which is preferably constantly monitoring the carrier with respect to changes in absorption, in fluorescence or in optical activity. According to the invention prior to being transported past the optical detector the carrier, which is comming from the separation zone, is directed through a refractive index equalizing unit, where its refractive index is preferably constantly monitored and where upon detection of changes of the refractive index of the carrier the deviation is compensated by adding to the carrier a compensating agent.

In a preferred embodiment of the invention the carrier is transported inside the refractive index equalizing unit through a refractive index detector, which is connected with a controller unit. Upon detection of a deviation of the refractive index of the carrier, the controller unit controls the amount of compensating fluid, which is added to the carrier via a mixing chamber arranged upstream the refractive index detector, until the nominal value of the refractive index of the carrier is reached again.

The flexibility of the inventive method is increased even more, if depending on the detection of positive or negative refractive index deviations, a controlled amount of compensating agent having a refractive index lower or higher respectively than the refractive index of the carrier is added.

An analytic separation arrangement according to the invention comprises a system of tubes including a separation zone, preferably a separation column, which tubes upstream the separation zone are connected with reservoirs for a carrier and a chemical sample to be separated and analyzed, and downstream the separation zone are connected with a waste container for the carrier containing the sample and also are connected with transporting means for the carrier and the sample. The tube system is associated with an optical detector for monitoring changes in the absorption, in the fluorescence or in the optical activity of the carrier when it is transported through the tube system and past the optical detector, which is arranged in the path of the carrier behind the separation zone but in front of the waste container. Between the separation zone and the optical detector there is arranged in the path of the carrier a refractive index equalizing unit.

In a preferred embodiment according to the invention the refractive index equalizing unit comprises a refractive index detector, a mixing chamber, which is arranged upstream the refractive index detector in the path of the carrier and is connected to a reservoir for a compensating agent, and a controller unit, which on the one hand is connected with the refractive index detector and on the other hand with a dispensing device associated with the reservoir for the compensating agent.

The flexibility of the analytical separation arrangement according to the invention is considerably increased if the mixing chamber is connected with two reservoirs for two kinds of compensating agents, one having a refractive index higher than the nominal value of the refractive index of the carrier and the other having a refractive index lower respectively. Thus it is possible to compensate a wide range of deviations from the nominal value of the refractive index of the carrier, positive deviations as well as negative ones. Preferably the refractive indices of the compensating agents differ considerably from the nominal value of the refractive index of the carrier.

It is advantageous for the sensitivity and the accuracy of the analytical separation arrangement, when the total active volume of the refractive index equalizing unit, comprised of the volumes of carrier in the mixing chamber, the refractive index detector and the tubing interconnecting these two elements, is smaller than the volume of the optical detector.

In a preferred embodiment of the invention the total active volume of the equalizer amounts from about 0.5 $\mu$l to about 1 ml, preferably to about 10 $\mu$l. In even more miniaturized embodiments of the invention, for example in on-chip realizations, the active volume of the equalizer can amount to as little as about 1 nl.

It is particularly advantageous that the set-up of the inventive analytical separation arrangement can be simplified by using low rate syringe pumps having a pumping rate from about 1 $\mu$l/min to about 100 $\mu$l/min as the dispensing devices.

It is to be noted that the set-up of the invention is even more simplified by the fact that the controller unit is an off-the-shelf microcomputer-controlled DC-motor controller for the syringe pumps.

BRIEF DESCRIPTION OF THE DRAWINGS

Further aspects and advantages of the invention will become apparent from the description of preferred embodiments of the invention, which are provided as non limiting illustrations, with respect to the accompanying drawings. In the drawings.

DESCRIPTION OF THE PREFERRED EMBODIMENT

Figure 1:
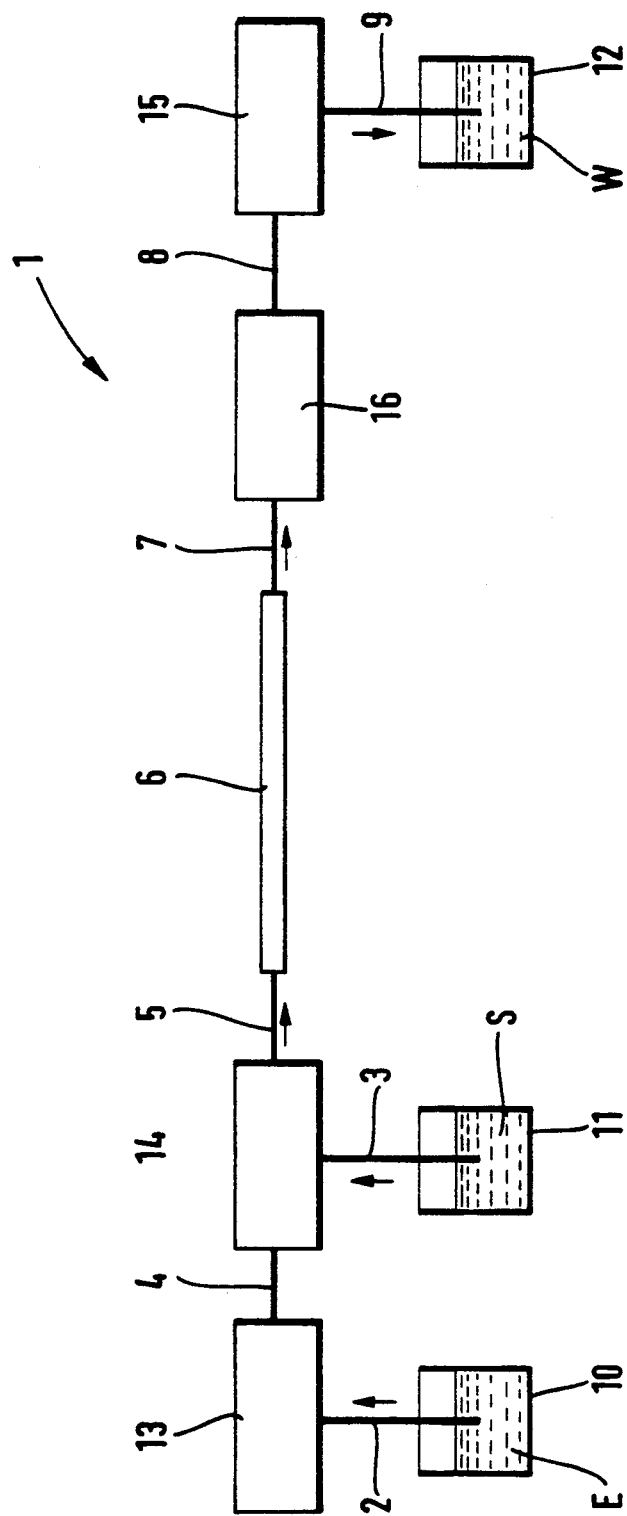
FIG. 1 shows schematically an analytic separation arrangement according to the invention.

In FIG. 1 an examplary embodiment of an analytic separation arrangement as employed in high performance liquid chromatography is drawn schematically and generally designated with reference numeral 1. It represents the arrangements used for example in liquid chromatography, in supercritical fluid chromatography, in high performance chromatography or even in capillary zone electrophoresis. The arrangement comprises a system of tubes 2 through 9 including a separation column 6. The separation column is of the packed type, as described for example in "Praxis der Hochleistungs-Flüssigchromatographie" by Veronika R. Meyer, published by Diesterweg Sauerländer, 5. Auflage, Frankfurt 1979. Upstream the separation column 6 the tube system is connected with a reservoir 10 for a carrier E and with a second reservoir 11 for a chemical sample S, which is to be separated and analyzed. Downstream the separation column 6 the tube system is connected with a waste container 12 for the carrier containing the sample, which mixture is generally depicted as waste W.

Transporting means 13 and 14 are provided to transport the carrier E through the tube system 2-9 and to inject a predetermined amount of the chemical sample S into the stream of the carrier E respectively. Preferably the transporting means 13 and 14 are dosing pumps, which allow to control the pumping rate. The transporting means 14 also comprises an injection valve (not shown) for introducing the chemical sample S into the carrier E. In order to reduce the volumes to be filled with the carrier E and also in order to reduce the amount of chemical sample S required for reasonable analytical results the system of tubes 2-9 preferably is comprised of capillary tubes having internal diameters less than or equal to about 300 $\mu$m. Thus dosing pumps having a pumping rate of about 1 ml/min are usually sufficient.

Instead of dosing pumps for the transport of the carrier E and the sample S there could also be provided electrodes communicating with the reservoirs 10 and 11 for the carrier E and the sample S respectively and with the waste container 12 to apply electric fields for the transportation of the agents. There could be provided additional electrodes communicating with the individual segments of the system of tubes 2-9, in order to be able to apply the electric field only segmentwise. Thus in spite of the limiting isolating properties of the materials used for the tubes the total electric field applied in the tube-system could be even increased.

Downstream the separation column 6 but before the end section 8,9 of the system of capillary tubes 2-9 ends in the waste container 12 an optical detector 15 is arranged in the path of the carrier E. The optical detector 15 is designed to monitor changes in the absorption, in the fluorescence or in the optical activity of the carrier. Such detector is described for example in U.S. Pat. No. 4,989,974, the subject matter of which is included herewith by reference. Thus far the analytic separating arrangement corresponds to those known from the prior art.

According to the invention between the separation column 6 and the optical detector 15 there is arranged in the path of the carrier E a refractive index equalizing unit 16. The set-up of a first exemplary embodiment of the refractive index equalizing unit is shown in more detail in FIG. 2. It comprises a refractive index detector 19, a mixing chamber 17, which is arranged in the path of the carrier E upstream the detector 19 and is connected to a reservoir 21 for a compensating agent C, and a tube 18 interconnecting the mixing chamber 17 and the detector 19. Further the equalizing unit comprises a controller unit 20, which is connected on the one hand with the refractive index detector and on the other hand with a dispensing device 22 associated via tubes 23 and 24 with the reservoir 21 and the mixing chamber 17 respectively.

In principle any refractive index detector could be used, however, in a preferred embodiment the refractive index equalizing unit 16 comprises a refractive index detector 19 as described for example in EP-A-0,440,577 or in A. E. Bruno et al. "On-Column Laser-Based Refractive Index Detector for Capillary Electrophoresis", Anal. Chem. 1991, 63, 2689-2697, the subject matter of which is included herewith by reference. The main demands on the refractive index detector are that its active volume is smaller than the volume of the separated component of the injected chemical sample S and that the response time is fast enough, to resolve and detect different components of the sample S, which pass the detector one after the other in short time intervals. Preferably the response time is less than 10 seconds. The mixing unit 17 must also have a small active volume, in order to avoid a spreading of the components in the carrier passing the mixer. Thus the best results are achieved with a refractive index equalizing unit 17 having a total active volume, which is comprised of the active volumes of the mixing chamber 17, of the refractive index detector 19 and of the interconnecting (capillary) tube 18, that is smaller than the volume of the optical detector 15. Here the active volumes are defined as the volumes of carrier E flowing through the respective elements 17, 18 and 19. In particular should the total volume of the refractive index equalizing unit 16 amount to from about 0.5 $\mu$l to about 1 ml, preferably to about 10 $\mu$l. In even more miniaturized embodiments of the invention, for example in on-chip realizations, the total active volume of the equalizer amounts to as little as about 1 nl.

Figure 3:
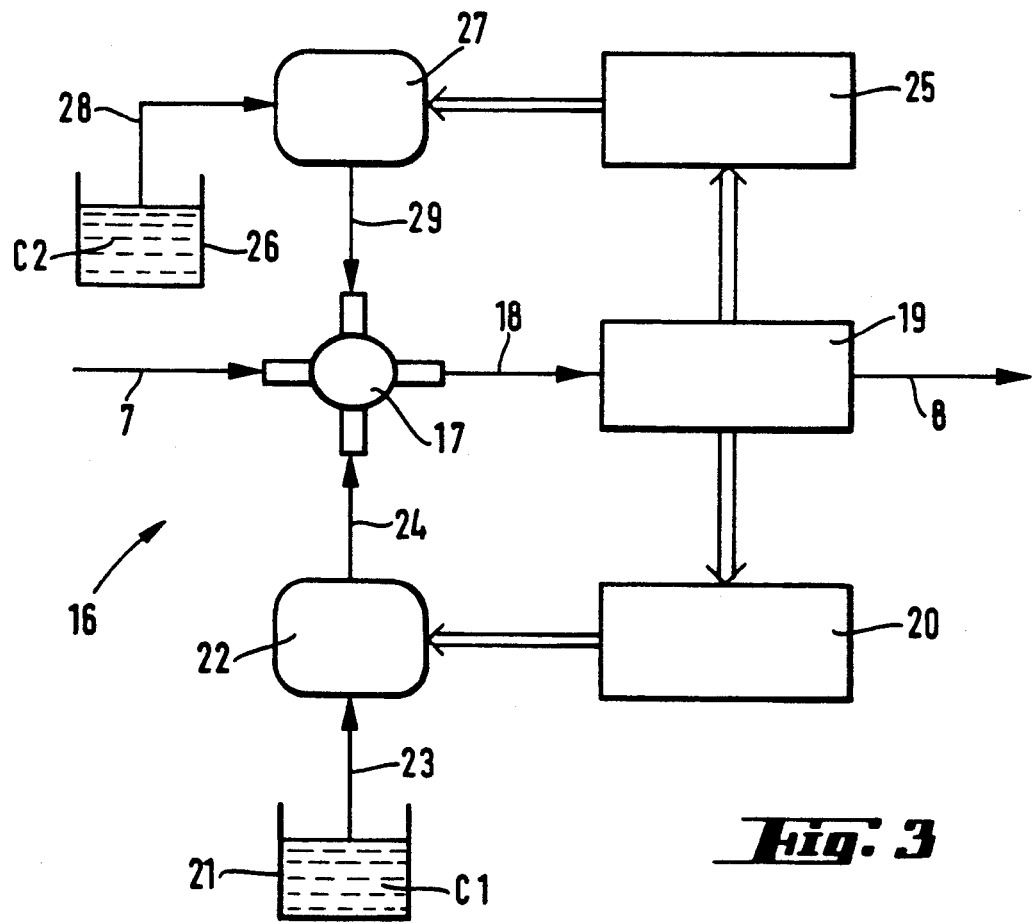
FIG. 3 shows a second embodiment of the refractive index equalizing unit.

FIG. 3 depicts an even more preferred second exemplary embodiment of the refractive index equalizing unit 16 of the analytical separation arrangement 1 according to the instant invention. In this embodiment there are provided two reservoirs 21 and 26 for two kinds of compensating agents C1 and C2, one having a refractive index higher than the nominal value of the refractive index of the carrier E and the other having a lower refractive index, which are connected with the mixing chamber 17. Correspondingly the refractive index equalizing unit 16 comprises two dispensing devices 22 and 27, which are associated with the two reservoirs 21 and 26 respectively. The refractive index detector 19 is connected with two controller units 20 and 25, each one controlling one of the two dispensing devices. It is to be understood that there could also be provided only one controller unit having two channels for controlling the two dispensing devices 22 and 27.

Preferably the dispensing devices 22 and 27 are low rate syringe pumps, which have an adjustable pumping rate from about 1 $\mu$l/min to about 100 $\mu$l/min. The controller unit 20 and 25 respectively is preferably a (micro)computer-controlled DC-motor controller for the syringe pumps.

It is to be noted, that very much similar to the possibility to transport the carrier and inject the chemical sample with the aid of electric fields, the compensating agents also could be introduced into the mixing chamber by applying electric fields between the respective reservoir and the mixing chamber. Thus the controller unit would not need to be a DC-controller any more, but it would be a controllable relays which could provide the necessary connections of the respective electrodes with a voltage-source. The amount of compensating agent could be regulated via the length of the period of time the electric field is applied. The necessary signals could be provided by a microcomputer, which is connected with the refractive index detector and the relays.

In a separation method for the analysis of chemical samples according to the instant invention prior to entering the separation column 6 the chemical sample S is introduced into the carrier E, which is transported through the system of tubes 2–9 and past the optical detector 15. After passing the separation column 6 the carrier E and the sample S, separated into its components, are transported past the optical detector 15, which is preferably constantly monitoring the carrier E with respect to changes in absorption, in fluorescence or in optical activity. Prior to being transported past the optical detector 15 the carrier E, which is comming from the separation column 6, is directed through the refractive index equalizing unit 16, where its refractive index is preferably constantly monitored and where upon detection of changes of the refractive index of the carrier E the deviation is compensated by adding to the carrier E a compensating agent C and C1 or C2 respectively.

By choosing compensating agents C or C1 and C2 respectively, having refractive indices, which show a large positive or negative difference to the nominal value of the refractive index of the carrier E, the range of possible compensations of refractive index deviations can be strongly increased. Of course, only compensating agents whose optical properties with respect to absorption, fluorescence or optical activity do not interfere with those of the chemical sample to be analysed are chosen.

Inside the refractive index equalizing unit the carrier E is transported through the refractive index detector 19, which is connected with the controller unit(s) 20 and 25 respectively. Upon detection of a deviation of the refractive index of the carrier E, the respective controller unit 20 or 25 controls the amount of compensating agent C and C1 or C2 respectively, which is added to the carrier E via the mixing chamber 17 arranged upstream the refractive index detector, until the nominal value of the refractive index of the carrier E is reached again.

The flexibility of the inventive method is increased and even doubled, if depending on the detection of positive or negative refractive index deviations, a controlled amount of compensating agent C1 or C2 having a refractive index lower or higher respectively than the refractive index of the carrier E is added.

Figure 2:
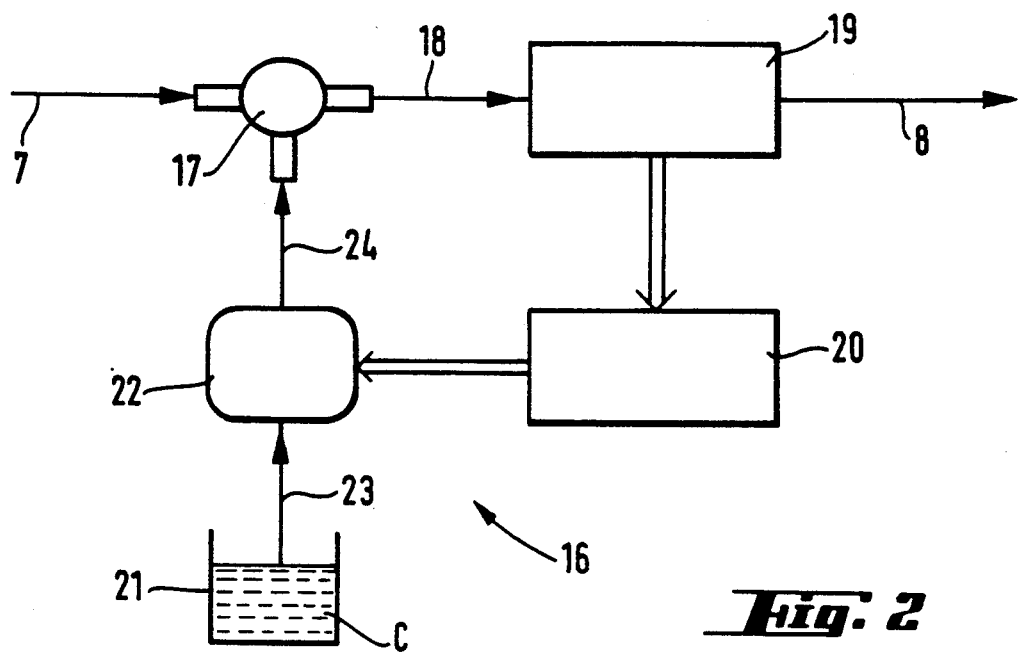
FIG. 2 shows a first embodiment of a refractive index equalizing unit.

In the exemplary embodiments of the invention as described with reference to the FIGS. 1–3 the variations of the refractive index of the carrier E are compensated by adding a definite amount of a compensating agent, preferably a compensating liquid C and C1 or C2 respectively. It is to be noted that the compensation of the refractive index changes can also be achieved by adding to the carrier E depending on the deviations detected a definite amount of for example sugars or salts or similar means soluble in the carrier and capable of changing its refractive index to a higher or lower value than detected. The compensation of the changes of the refractive index of the carrier E can also be achieved by changing for example the temperature or the pressure of the carrier E in a controlled manner depending on the refractive index deviations detected.

The following example serves to illustrate the separation method according to the instant invention in even more detail.

EXAMPLE

Figure 4:
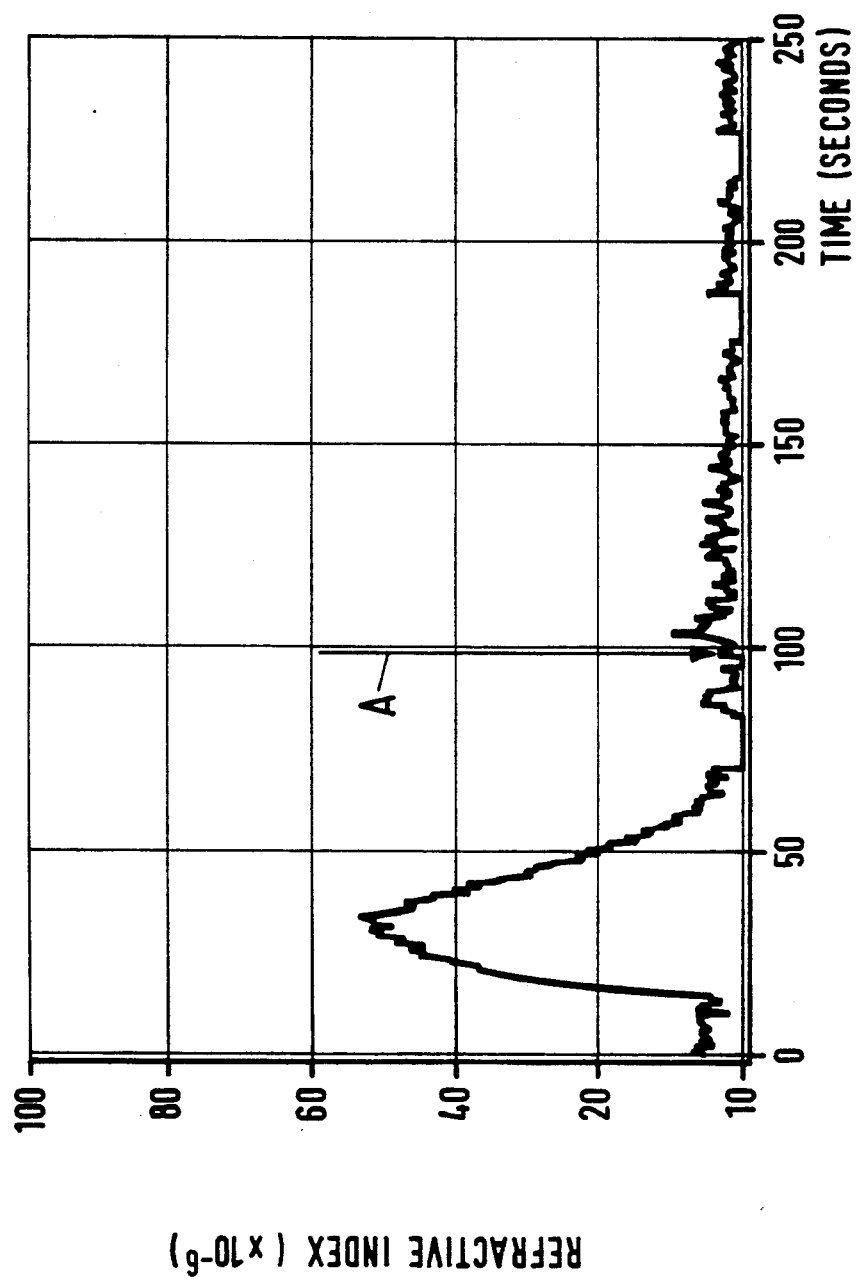
FIG. 4 is a diagram to explain the results achieved with the invention.

In order to stimulate the system in HPLC-like conditions, a simple Flow-Injection-Analysis system is constructed. To obtain high refractive index changes 500 $\mu$l of a sugar solution (0.05% sucrose in water) are injected into a constant flow of water having a flow rate inside the tube-system of 0.5 ml/min. The dimensions of the tube-system made of glass capillaries is chosen to produce a signal response at the optical detector, which is very much similar to those observed in HPLC-analysis. A capillary refractive index detector, as described Analytical Chemistry 1989, 61, pages 876–883, with a total active volume of about 6 $\mu$l is used together with a mixing chamber of about 10 $\mu$l, which is described for example in prospectus No. 411 7306141 by the company Brechbuehler AG of Switzerland. The dispensing device is a low rate syringe pump. The controller unit is an off-the-shelf DC-motor regulator. The compensating agent has a high refractive index in comparison to the injected sugar solution and is comprised of 0.5% sucrose in water. Two identical injections are performed successively. The results are depicted in FIG. 4. In the first part of the diagramm the first injection without activation of the refractive index equalizing unit is shown. The large peak indicates a large deviation of the refractive index. After about a 100 seconds, the refractive index equalizing unit is activated (symbolized by the arrow A in FIG. 4) and the second injection is performed. By adding the compensating agent the hights of the peaks are considerably reduced, resulting in refractive index variations corresponding to the natural variations of the quality and purity of the carrier. Thus the influences of refractive index variations in successive optical measurements can be efficiently reduced and even be eliminated.

While preferred embodiments of the invention have been shown, it will be understood that the invention may be embodied otherwise as herein specifically illustrated or described, and that certain changes in the form and arrangement of elements and in the specific manner of practising the invention may be made without departing from the underlying ideas or principles of this invention within the scope of the appended claims.

What is claimed is:

1. An analytic separation arrangement comprising:
   a) a first reservoir containing a carrier having a nominal refractive index;
   b) a second reservoir containing a chemical sample;
   c) separating means for separating a sample into components;
   d) refractive index equalizing means for controlling the refractive index of the carrier by detecting the refractive index of the carrier and adding a compensating agent to the carrier in response to the detected refractive index;
   e) an optical detector for monitoring the absorption, fluorescence or optical activity of the carrier;
   f) a waste container; and
   g) transporting means for transporting the carrier from the first reservoir to the separating means, introducing the sample into the carrier between the first reservoir and the separating means, and transporting the carrier in series, via connecting tubes, through the separation means, the refractive index equalizing means, the optical detector, and into the waste container.

2. An analytic separation arrangement according to claim 1, wherein the separating means is a separation column.

3. An analytic separation arrangement according to claim 1 wherein said refractive index equalizing means includes:
   a refractive index detector,
   a mixing chamber which is connected to a third reservoir containing said compensating agent,
   a first dispensing device connected to said third reservoir containing said compensating agent, and
   first controlling means for controlling said first dispensing device which is connected with both said refractive index detector and the first dispensing device,
   wherein the refractive index detector and mixing chamber are arranged such that the carrier passes first through the mixing chamber and then through the refractive index detector.

4. An analytical arrangement according to claim 3, wherein the refractive index equalizing means includes:
   a second dispensing device,
   a fourth reservoir connected to said second dispensing device and to said mixing chamber, said fourth reservoir containing an additional compensating agent different from the compensating agent in the third reservoir,
   a second controlling means for controlling said second dispensing device which is connected with both said refractive index detector and the second dispensing device,
   wherein one of said compensating agent and said additional compensating agent has a refractive index higher than the nominal refractive index of said carrier and the other of said compensating agent and said additional compensating agent has a refractive index lower than the nominal refractive index of said carrier.

5. An analytical separation arrangement according to claim 4, wherein said first and second dispensing devices are syringe pumps having a pumping rate from about 1 $\mu$l/min to about 100 $\mu$l/min.

6. An analytical separation arrangement according to claim 5, wherein said first and second controlling means comprise a microcomputer-controlled DC-motor controller for said syringe pumps.

7. An analytical separation arrangement according to claim 4, wherein the mixing chamber and the refractive index detector are interconnected with a length of tubing;
   the mixing chamber, the refractive index detector, the length of tubing, and the optical detector each have a volume;
   said refractive index equalizing means has a total active volume, which is defined as the sum of the volumes of said mixing chamber, said refractive index detector and said length of tubing; and
   the total active volume of the refractive index equalizing means is smaller than the volume of said optical detector.

8. An analytical separation arrangement according to claim 7, wherein said total active volume of said refractive index equalizing means amounts to from about 0.5 $\mu$l to about 1 ml.

9. An analytical separation arrangement according to claim 8, wherein the total active volume is about 10 $\mu$l.

* * * * *